United States Patent
Hayböck et al.

(10) Patent No.: US 11,959,918 B2
(45) Date of Patent: Apr. 16, 2024

(54) EUKARYOTIC TRANSLATION INITIATION FACTORS (eIFs) AS NOVEL BIOMARKERS IN BLADDER CANCER

(71) Applicant: Otto-von-Guericke-Universität Magdeburg, Magdeburg (DE)

(72) Inventors: Johannes Haybäck, Innsbruck (AT); Jeton Luzha, Magdeburg (DE)

(73) Assignee: OTTO-VON-GUERICKE-UNIVERSITÄT MAGDEBURG, Magdeburg (DE)

( * ) Notice: Subject to any disclaimer, the term of this patent is extended or adjusted under 35 U.S.C. 154(b) by 263 days.

(21) Appl. No.: 16/911,226

(22) Filed: Jun. 24, 2020

(65) Prior Publication Data
US 2021/0025891 A1   Jan. 28, 2021

(30) Foreign Application Priority Data

Jul. 23, 2019  (EP) .................................... 19187871

(51) Int. Cl.
| | |
|---|---|
| G01N 33/00 | (2006.01) |
| A61K 39/00 | (2006.01) |
| C07K 16/32 | (2006.01) |
| G01N 33/53 | (2006.01) |
| G01N 33/574 | (2006.01) |
| G01N 33/68 | (2006.01) |

(52) U.S. Cl.
CPC ....... *G01N 33/57484* (2013.01); *C07K 16/32* (2013.01); *G01N 33/5302* (2013.01); *G01N 33/57407* (2013.01); *G01N 33/6872* (2013.01)

(58) Field of Classification Search
CPC ......... G01N 33/57484; G01N 33/5302; G01N 33/57407; G01N 33/6872; C07K 16/32
See application file for complete search history.

(56) References Cited

FOREIGN PATENT DOCUMENTS

WO    2018/024608 A2    2/2018

OTHER PUBLICATIONS

Ali et al (review article: Tumor Biology Jun. 2017: p. 1-19 (Year: 2017).*
Ali et al, Review, Tumor Biology, Jun. 2017: 1-19) (Year: 2017).*
Horvilleur et al (Leukemia 28:1092-1102, 2014 (Year: 2014).*
Crew et al (British J of Cancer 82: 161-166, 2000 (Year: 2000).*
Wang et al (Impactjournals.com/Oncotarget 7, No. 38, p. 62327-39, 2016 (Year: 2016).*
Sbarrato et al, Atlas of Genetic and Cytogenetics in Oncology and Haematoloty, Apr. 2014 (Year: 2014).*
Nicole Golob Schwarl, et al., "11 Supplementary Materials for Separation of low and high grade colon and rectum carcinoma by eukaryotic translation initiation factors I, 5 and 611," Oncotarget, Jan. 1, 2017 (Jan. 1, 2017), pp. 1-43.
Rita Spilka, et al., "11 eIF3a is over-expressed in urinary bladder cancer and influences its phenotype independent of translation initiation 11," Cellular Oncology, Springer, Dordrecht, vol. 37, No. 4, Jul. 29, 2014 (Jul. 29, 2014), pp. 253-267.
W. Chen, et al., 11 Overexpression of EIF-5A2 1-9, Is an Independent Predictor of Outcome in 11-13 Patients of Urothelial Carcinoma of the Bladder Treated with Radical Cystectomy 11, Cancer Epidemiology, Biomarkers And Prevention, vol. 18, No. 2, Feb. 3, 2009 (Feb. 3, 2009), pp. 400-408.
Jun-Hang Luo, et al., 11 Overexpression of EIF-5A2 predicts tumor recurrence and progression in pTa/pTI urothelial carcinoma of the bladder 11, Cancer Science, vol. 100, No. 5, Feb. 26, 2009 (Feb. 26, 2009), pp. 896-902.
JP Crew, "Eukaryotic initiation factor-4E in superficial and muscle invasive bladder cancer and its correlation with vascular endothelial growth factor expression and tumour progression", British Journal Of Cancer, vol. 82, No. I, Jan. 1, 2000 (Jan. 1, 2000), pp. 161-166.
Bang-Fen Zhou, et al., "Identification and validation of AIBI and EIF5A2 for noninvasive detection of bladder cancer in urine samples", Oncotarget, vol. 7, No. 27, Jul. 5, 2016 (Jul. 5, 2016), p. 27.
Partial European Search Report dated Jan. 14, 2020 in European Patent Application No. EP 19 18 7871. 16 pages.

* cited by examiner

*Primary Examiner* — Lei Yao

(74) *Attorney, Agent, or Firm* — Kilpatrick Townsend & Stockton LLP

(57) ABSTRACT

The present invention relates to a method of diagnosing bladder cancer in an individual. Further, the present invention relates to a method of determining the course of bladder cancer in an individual. Furthermore, the present invention relates to a kit for diagnosing bladder cancer in an individual or determining the course of bladder cancer in an individual.

11 Claims, 26 Drawing Sheets

FIGURE 3A
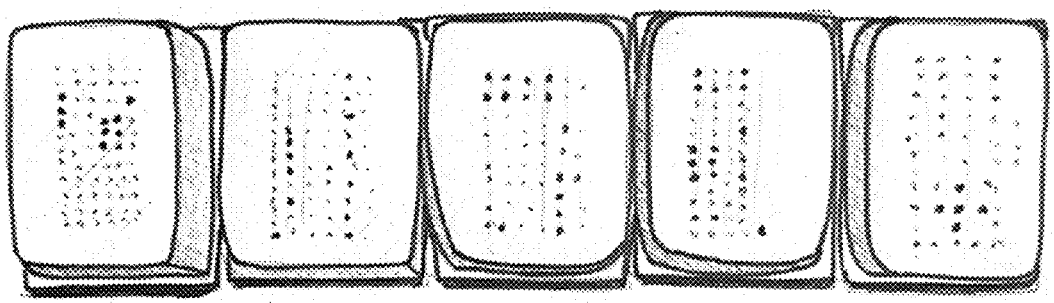
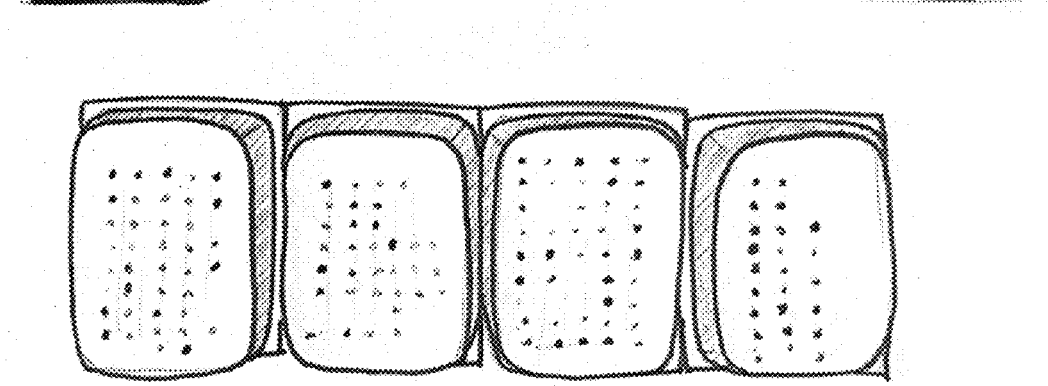
FIGURE 3B eIF1

NPar Tests
NPar Tests - Descriptive Statistics

Descriptive Statistics

| | N | Mean | Std. Deviation | Minimum | Maximum | Percentiles | | |
|---|---|---|---|---|---|---|---|---|
| | | | | | | 25th | 50th (Median) | 75th |
| eIF1-CO T | 103 | .23 | .447 | 0 | 2 | .00 | .00 | .00 |
| eIF1-CO NT | 79 | .753 | .6776 | .0 | 2.0 | .000 | 1.000 | 1.000 |

FIGURE 4A

Wilcoxon Signed Ranks Test

Wilcoxon Signed Ranks Test - Test Statistics

Test Statistics[a]

|  | eIF1-C 0 NT I - eIF1-C 0 I |
|---|---|
| Z | -5.424[b] |
| Asymp. Sig. (2-tailed) | .000 | a. Wilcoxon Signed Ranks Test
b. Based on negative ranks.

FIGURE 4C eIF4B

NPar Tests
NPar Tests - Descriptive Statistics

Descriptive Statistics

| | N | Mean | Std. Deviation | Minimum | Maximum | Percentiles | | |
|---|---|---|---|---|---|---|---|---|
| | | | | | | 25th | 50th (Median) | 75th |
| eIF4b CO | 105 | 1.56 | .619 | 0 | 3 | 1.00 | 2.00 | 2.00 |
| eIF4b CONT | 75 | 1.093 | .6763 | .0 | 2.0 | 1.000 | 1.000 | 1.500 |

FIGURE 5A

Wilcoxon Signed Ranks Test
Wilcoxon Signed Ranks Test - Test Statistics

Test Statistics[a]

| | eIF4b-C 0 NT I - eIF4b-C 0 I |
|---|---|
| Z | -3.692[b] |
| Asymp. Sig. (2-tailed) | .000 | a. Wilcoxon Signed Ranks Test
b. Based on positive ranks.

FIGURE 5C eIF4G

NPar Tests
NPar Tests - Descriptive Statistics

Descriptive Statistics

|  | N | Mean | Std. Deviation | Minimum | Maximum | Percentiles 25th | Percentiles 50th (Median) | Percentiles 75th |
|---|---|---|---|---|---|---|---|---|
| eIF4g-CO | 105 | 2.27 | .750 | 0 | 3 | 2.00 | 2.00 | 3.00 |
| eIF4g-CONT | 73 | 1.562 | 1.1363 | .0 | 3.0 | .000 | 2.000 | 2.500 |

FIGURE 6A

Wilcoxon Signed Ranks Test

Wilcoxon Signed Ranks Test - Test Statistics

Test Statistics[a]

|  | eIF4g-C O NT I - eIF4g-C O I |
|---|---|
| Z | -4.019[b] |
| Asymp. Sig. (2-tailed) | .000 | a. Wilcoxon Signed Ranks Test
b. Based on positive ranks.

FIGURE 6C eIF5A

NPar Tests
NPar Tests - Descriptive Statistics

Descriptive Statistics

| | N | Mean | Std. Deviation | Minimum | Maximum | Percentiles | | |
|---|---|---|---|---|---|---|---|---|
| | | | | | | 25th | 50th (Median) | 75th |
| eIF5a-CO | 105 | 1.19 | .761 | 0 | 3 | 1.00 | 1.00 | 2.00 |
| eIF5a-CONT | 72 | 1.479 | .7847 | .0 | 3.0 | 1.000 | 2.000 | 2.000 |

FIGURE 7A

Wilcoxon Signed Ranks Test
Wilcoxon Signed Ranks Test - Test Statistics

Test Statistics[a]

| | eIF5a-C 0 NT 1 - eIF5a-C 0 1 |
|---|---|
| Z | -2.780[b] |
| Asymp. Sig. (2-tailed) | .005 | a. Wilcoxon Signed Ranks Test
b. Based on negative ranks.

FIGURE 7C eIF5B

NPar Tests
NPar Tests - Descriptive Statistics

Descriptive Statistics

| | N | Mean | Std. Deviation | Minimum | Maximum | Percentiles | | |
|---|---|---|---|---|---|---|---|---|
| | | | | | | 25th | 50th (Median) | 75th |
| eIF5b C 01 | 105 | 1.81 | .722 | 0 | 3 | 1.00 | 2.00 | 2.00 |
| eIF5b C 0 NT | 74 | 1.250 | .8937 | .0 | 3.0 | 1.000 | 1.000 | 2.000 |

FIGURE 8A

Wilcoxon Signed Ranks Test

Wilcoxon Signed Ranks Test - Test Statistics

Test Statistics[a]

|  | eIF5b-C 0 NT I - eIF5b-C 0 I |
|---|---|
| Z | -4.219[b] |
| Asymp. Sig. (2-tailed) | .000 | a. Wilcoxon Signed Ranks Test
b. Based on positive ranks.

FIGURE 8C eIF6

NPar Tests
NPar Tests - Descriptive Statistics

Descriptive Statistics

| | N | Mean | Std. Deviation | Minimum | Maximum | Percentiles | | |
|---|---|---|---|---|---|---|---|---|
| | | | | | | 25th | 50th (Median) | 75th |
| eIF6-CO | 104 | 2.56 | .666 | 0 | 3 | 2.00 | 3.00 | 3.00 |
| eIF6-CONT | 74 | 1.716 | 1.1360 | 0 | 3.0 | .375 | 2.000 | 3.000 |

FIGURE 9A

Wilcoxon Signed Ranks Test

Wilcoxon Signed Ranks Test - Test Statistics

Test Statistics[a]

|  | eIF6-C 0 NT 1 - eIF6-C 0 1 |
|---|---|
| Z | -4.491[b] |
| Asymp. Sig. (2-tailed) | .000 | a. Wilcoxon Signed Ranks Test
b. Based on positive ranks.

FIGURE 9C

| No. | eIF1 | eIF5A | eIF4B | eIF4G | eIF5B |
|---|---|---|---|---|---|
|  |  |  |  |  |  |
| 1 |  |  |  |  |  |
| 2 |  |  |  |  | eIF5B |
| 3 |  |  |  |  | eIF5B |
| 4 |  |  |  | eIF4G |  |
| 5 |  |  |  | eIF4G |  |
| 6 |  |  |  | eIF4G | eIF5B |
| 7 |  |  |  | eIF4G | eIF5B |
| 8 |  |  | eIF4B |  |  |
| 9 |  |  | eIF4B |  |  |
| 10 |  |  | eIF4B |  | eIF5B |
| 11 |  |  | eIF4B |  | eIF5B |
| 12 |  |  | eIF4B | eIF4G |  |
| 13 |  |  | eIF4B | eIF4G |  |
| 14 |  |  | eIF4B | eIF4G | eIF5B |
| 15 |  |  | eIF4B | eIF4G | eIF5B |
| 16 |  | eIF5A |  |  |  |
| 17 |  | eIF5A |  |  |  |
| 18 |  | eIF5A |  |  | eIF5B |
| 19 |  | eIF5A |  |  | eIF5B |
| 20 |  | eIF5A |  | eIF4G |  |
| 21 |  | eIF5A |  | eIF4G |  |
| 22 |  | eIF5A |  | eIF4G | eIF5B |
| 23 |  | eIF5A |  | eIF4G | eIF5B |
| 24 |  | eIF5A | eIF4B |  |  |
| 25 |  | eIF5A | eIF4B |  |  |
| 26 |  | eIF5A | eIF4B |  | eIF5B |
| 27 |  | eIF5A | eIF4B |  | eIF5B |
| 28 |  | eIF5A | eIF4B | eIF4G |  |
| 29 |  | eIF5A | eIF4B | eIF4G |  |
| 30 |  | eIF5A | eIF4B | eIF4G | eIF5B |

FIGURE 10

| 31 |  | eIF5A | eIF4B | eIF4G | eIF5B |
|---|---|---|---|---|---|
| 32 | eIF1 |  |  |  |  |
| 33 | eIF1 |  |  |  |  |
| 34 | eIF1 |  |  |  | eIF5B |
| 35 | eIF1 |  |  |  | eIF5B |
| 36 | eIF1 |  |  | eIF4G |  |
| 37 | eIF1 |  |  | eIF4G |  |
| 38 | eIF1 |  |  | eIF4G | eIF5B |
| 39 | eIF1 |  |  | eIF4G | eIF5B |
| 40 | eIF1 |  | eIF4B |  |  |
| 41 | eIF1 |  | eIF4B |  |  |
| 42 | eIF1 |  | eIF4B |  | eIF5B |
| 43 | eIF1 |  | eIF4B |  | eIF5B |
| 44 | eIF1 |  | eIF4B | eIF4G |  |
| 45 | eIF1 |  | eIF4B | eIF4G |  |
| 46 | eIF1 |  | eIF4B | eIF4G | eIF5B |
| 47 | eIF1 |  | eIF4B | eIF4G | eIF5B |
| 48 | eIF1 | eIF5A |  |  |  |
| 49 | eIF1 | eIF5A |  |  |  |
| 50 | eIF1 | eIF5A |  |  | eIF5B |
| 51 | eIF1 | eIF5A |  |  | eIF5B |
| 52 | eIF1 | eIF5A |  | eIF4G |  |
| 53 | eIF1 | eIF5A |  | eIF4G |  |
| 54 | eIF1 | eIF5A |  | eIF4G | eIF5B |
| 55 | eIF1 | eIF5A |  | eIF4G | eIF5B |
| 56 | eIF1 | eIF5A | eIF4B |  |  |
| 57 | eIF1 | eIF5A | eIF4B |  |  |
| 58 | eIF1 | eIF5A | eIF4B |  | eIF5B |
| 59 | eIF1 | eIF5A | eIF4B |  | eIF5B |
| 60 | eIF1 | eIF5A | eIF4B | eIF4G |  |

FIGURE 10 (Cont.)

| | | | | | |
|---|---|---|---|---|---|
| 61 | eIF1 | eIF5A | eIF4B | eIF4G | |
| 62 | eIF1 | eIF5A | eIF4B | eIF4G | eIF5B |
| 63 | eIF1 | eIF5A | eIF4B | eIF4G | eIF5B |
| | | | | | |
| | | | | | |
| | | | | | eIF5B |
| | | | | | eIF5B |
| | | | | eIF4G | |
| | | | | eIF4G | |
| | | | | eIF4G | eIF5B |
| | | | | eIF4G | eIF5B |
| | | | eIF4B | | |
| | | | eIF4B | | |
| | | | eIF4B | | eIF5B |
| | | | eIF4B | | eIF5B |
| | | | eIF4B | eIF4G | |
| | | | eIF4B | eIF4G | |
| | | | eIF4B | eIF4G | eIF5B |
| | | | eIF4B | eIF4G | eIF5B |
| | | eIF5A | | | |
| | | eIF5A | | | |
| | | eIF5A | | | eIF5B |
| | | eIF5A | | | eIF5B |
| | | eIF5A | | eIF4G | |
| | | eIF5A | | eIF4G | |
| | | eIF5A | | eIF4G | eIF5B |
| | | eIF5A | | eIF4G | eIF5B |

FIGURE 10 (Cont.)

| | | | | | |
|---|---|---|---|---|---|
| | | eIF5A | eIF4B | | |
| | | eIF5A | eIF4B | | |
| | | eIF5A | eIF4B | | eIF5B |
| | | eIF5A | eIF4B | | eIF5B |
| | | eIF5A | eIF4B | eIF4G | |
| | | eIF5A | eIF4B | eIF4G | |
| | | eIF5A | eIF4B | eIF4G | eIF5B |
| | | eIF5A | eIF4B | eIF4G | eIF5B |
| | eIF1 | | | | |
| | eIF1 | | | | |
| | eIF1 | | | | eIF5B |
| | eIF1 | | | | eIF5B |
| | eIF1 | | | eIF4G | |
| | eIF1 | | | eIF4G | |
| | eIF1 | | | eIF4G | eIF5B |
| | eIF1 | | | eIF4G | eIF5B |
| | eIF1 | | eIF4B | | |
| | eIF1 | | eIF4B | | |
| | eIF1 | | eIF4B | | eIF5B |
| | eIF1 | | eIF4B | | eIF5B |
| | eIF1 | | eIF4B | eIF4G | |
| | eIF1 | | eIF4B | eIF4G | |
| | eIF1 | | eIF4B | eIF4G | eIF5B |
| | eIF1 | | eIF4B | eIF4G | eIF5B |

FIGURE 10 (Cont.)

| | eIF1 | eIF5A | | | |
|---|---|---|---|---|---|
| | eIF1 | eIF5A | | | |
| | eIF1 | eIF5A | | | eIF5B |
| | eIF1 | eIF5A | | | eIF5B |
| | eIF1 | eIF5A | | eIF4G | |
| | eIF1 | eIF5A | | eIF4G | |
| | eIF1 | eIF5A | | eIF4G | eIF5B |
| | eIF1 | eIF5A | | eIF4G | eIF5B |
| | eIF1 | eIF5A | eIF4B | | |
| | eIF1 | eIF5A | eIF4B | | |
| | eIF1 | eIF5A | eIF4B | | eIF5B |
| | eIF1 | eIF5A | eIF4B | | eIF5B |
| | eIF1 | eIF5A | eIF4B | eIF4G | |
| | eIF1 | eIF5A | eIF4B | eIF4G | |
| | eIF1 | eIF5A | eIF4B | eIF4G | eIF5B |
| | eIF1 | eIF5A | eIF4B | eIF4G | eIF5B |

FIGURE 10 (Cont.)

EUKARYOTIC TRANSLATION INITIATION FACTORS (eIFs) AS NOVEL BIOMARKERS IN BLADDER CANCER

The present invention relates to a method of diagnosing bladder cancer in an individual. Further, the present invention relates to a method of determining the course of bladder cancer in an individual. Furthermore, the present invention relates to a kit for diagnosing bladder cancer in an individual or determining the course of bladder cancer in an individual.

BACKGROUND OF THE INVENTION

Bladder cancer is the second most common genitourinary malignancy and represents the $9^{th}$ most common cancer worldwide and the $4^{th}$ common cancer in men in the United States. It is a very heterogeneous disease which is really challenging to the treating clinician. Bladder cancer arises from the tissues of the urinary bladder. It is a disease in which cells grow abnormally and have the potential to spread to other parts of the body. Symptoms of bladder cancer include blood in the urine, pain with urination, and low back pain. Risk factors for bladder cancer include smoking, family history, prior radiation therapy, frequent bladder infections, and exposure to certain chemicals. The most common type is urinary bladder cancer (UBC) (also designated as transitional cell carcinoma). Other types include squamous cell carcinoma and adenocarcinoma.

Diagnosis of bladder cancer is typically by cystoscopy with tissue biopsy. Staging of the cancer is typically determined by medical imaging such as Computer tomography (CT) scan and bone scan. Treatment depends on the stage of the cancer. It may include drug administration, surgery, radiation therapy, chemotherapy, and/or immunotherapy. Surgical options may include transurethral resection, partial or complete removal of the bladder, or urinary diversion. Typical five-year survival rates in the United States are 77%.

Urinary bladder cancer (UBC) is the most common histology of the bladder cancer and is associated with high mortality rates and poor prognosis. Painless hematuria and other signs and symptoms of UBC are not specific and often arise at late stage of disease. For this reason, diagnosis is typically made when the cancer is already in advanced stages and prognosis for survival is bad.

The diagnosis of bladder cancer remains modest. Thus, new biomarkers for diagnosing bladder cancer and for monitoring disease progression are strongly required. Commonly, dysregulated protein synthesis contributes to carcinogenesis and cancer progression. In this case, protein synthesis directs translation of specific mRNAs and, in turn, promotes cell survival, invasion, angiogenesis, and metastasis of tumors. In eukaryotes, protein synthesis is regulated at its initiation, which is a rate-limiting step involving eukaryotic translation initiation factors (eIFs).

The present inventors examined the performance of eukaryotic translation initiation factors (eIFs) in bladder cancer. They ascertained that eIFs represent crossroads in the development of bladder cancer and can serve as biomarkers for bladder cancer. In particular, the present inventors found that eIFs are deregulated between patients suffering from UBC and healthy individuals. They identified with eIF1, eIF5A, eIF4B eIF4G, eIF5B, eIF6, and eIF3H new diagnostic biomarkers for UBC. These new diagnostic biomarkers allow the diagnosis and monitoring of UBC. Immunohistochemical data from tissue microarray (n=107) demonstrated significantly higher expression levels of eIF4B eIF4G, eIF5B, and eIF6 in patients suffering from UBC compared to non-neoplastic tissue (healthy controls). In contrast thereto, eIF1 and eIF5A were significantly downregulated in patients suffering from UBC compared to non-neoplastic tissue (healthy controls). eIF3H was also downregulated in patients suffering from UBC compared to non-neoplastic tissue (healthy controls). Thus, these new diagnostic biomarkers allow quick and accurate clinical diagnostics.

SUMMARY OF THE INVENTION

In a first aspect, the present invention relates to a method of diagnosing bladder cancer in an individual (suspected of having bladder cancer) comprising the step of:
determining the level of at least one eukaryotic Initiation Factor (eIF) in a sample from an individual,
wherein the at least one eIF is selected from the group consisting of eIF1, eIF5A, eIF4B, eIF4G, eIF5B, eIF6, and eIF3H.

In a second aspect, the present invention relates to a method of determining the course of bladder cancer in an individual (suffering from bladder cancer) comprising the step of:
determining the level of at least one eukaryotic Initiation Factor (eIF) in a sample from an individual,
wherein the at least one eIF is selected from the group consisting of eIF1, eIF5A, eIF4B, eIF4G, eIF5B, eIF6, and eIF3H.

In a third aspect, the present invention relates to the use of at least one eIF for diagnosing bladder cancer in an individual (suspected of having bladder cancer) or determining the course of bladder cancer in an individual (suffering from bladder cancer),
wherein the at least one eIF is selected from the group consisting of eIF1, eIF5A, eIF4B, eIF4G, eIF5B, eIF6, and eIF3H.

In a fourth aspect, the present invention relates to a kit for diagnosing bladder cancer in an individual (suspected of having bladder cancer) or determining the course of bladder cancer in an individual (suffering from bladder cancer) comprising
means for determining the level of at least one eIF in a sample from an individual, wherein the at least one eIF is selected from the group consisting of eIF1, eIF5A, eIF4B, eIF4G, eIF5B, eIF6, and eIF3H.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU- PAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "bladder cancer", as used herein, refers to a type of cancer arising from the tissues of the urinary bladder. It is a disease in which cells grow abnormally and have the potential to spread to other parts of the body. Symptoms of bladder cancer include blood in the urine, pain with urination, and low back pain. Risk factors for bladder cancer include smoking, family history, prior radiation therapy, frequent bladder infections, and exposure to certain chemicals. The most common type is urinary bladder cancer (UBC) (also designated as transitional cell carcinoma). Other types include squamous cell carcinoma and adenocarcinoma.

The treatment of bladder cancer include, but is not limited to, drug therapy/administration, surgery, radiation therapy, chemotherapy, and/or immunotherapy. Surgical options may include transurethral resection, partial or complete removal of the bladder, or urinary diversion.

Preferably, the bladder cancer is selected from the group consisting of urothelial bladder cancer (UBC) (also designated as transitional cell bladder cancer), squamous cell bladder cancer, adenocarcinoma, sarcoma, and small cell bladder cancer. More preferably, the bladder cancer is UBC.

The term "diagnosing bladder cancer", as used herein, means determining whether an individual shows signs of or suffers from bladder cancer.

The term "determining the course of bladder cancer", as used herein, means determining the development of bladder cancer over time, e.g. whether bladder cancer worsens in the individual, does not worsen/is stable in the individual, or improves in the individual over time.

The term "individual", as used herein, refers to any subject for whom it is desired to know whether she or he suffers from bladder cancer. In particular, the term "individual", as used herein, refers to a subject suspected to be affected by bladder cancer. The individual may be diagnosed to be affected by bladder cancer, i.e. diseased, or may be diagnosed to be not affected by bladder cancer, i.e. healthy. The term "individual", as used herein, also refers to a subject which is affected by bladder cancer, i.e. diseased. The patient may be retested for bladder cancer and may be diagnosed to be still affected by bladder cancer, i.e. diseased, or not affected by bladder cancer anymore, i.e. healthy, for example after therapeutic intervention. The individual may have developed an advanced form of bladder cancer. For example, it may be determined that bladder cancer worsened, not worsened/is stable, or improved in the individual (over time). It should be noted that an individual that is diagnosed as being healthy, i.e. not suffering from bladder cancer, may possibly suffer from another disease or condition not tested/known. The individual may be any mammal, including both a human and another mammal, e.g. an animal such as a rabbit, mouse, rat, or monkey. Human individuals are particularly preferred.

The term "(control) patient", as used herein, refers to a subject known to be affected by bladder cancer (positive control), i.e. diseased. Said (control) patient may have developed an advanced form of bladder cancer.

The (control) patient may be any mammal, including both a human and another mammal, e.g. an animal such as a rabbit, mouse, rat, or monkey. Human (control) patients are particularly preferred.

The term "healthy (control) individual/subject", as used herein, refers to a subject known to be not affected by bladder cancer (negative control), i.e. healthy.

It should be noted that an individual which is known to be healthy, i.e. not suffering from bladder cancer, may possibly suffer from another disease or condition not tested/known. The healthy individual may be any mammal, including both a human and another mammal, e.g. an animal such as a rabbit, mouse, rat, or monkey. Human healthy individuals are particularly preferred.

The term "treatment", in particular "therapeutic treatment", as used herein, refers to any therapy which improves the health status and/or prolongs (increases) the lifespan of an individual suffering from a disease or condition, in particular a tumor. Said therapy may eliminate the disease or condition in an individual, arrest or slow the development of a disease in an individual, inhibit or slow the development of a disease in an individual, decrease the frequency or severity of symptoms in an individual, and/or decrease the recurrence in an individual who currently has or who previously has had a disease. The treatment of bladder cancer is preferably selected from the group consisting of the administration of a drug, surgery, chemotherapy, radiotherapy, and a combination thereof.

The term "level", as used herein, refers to an amount (measured for example in grams, mole, or ion counts) or concentration (e.g. absolute or relative concentration) of the at least one eIF claimed herein. The term "level", as used herein, also comprises scaled, normalized, or scaled and normalized amounts or values. The level may also be a cut-off level. In one embodiment, the level is an expression level.

The term "eukaryotic Initiation Factor (eIF)", as used herein, refers to molecules which are involved in the initiation phase of eukaryotic translation. These factors help to stabilize the formation of the functional ribosome around the start codon and also provide regulatory mechanisms in translation initiation. The following eIFs are mentioned in the context of the present invention: eIF1, eIF5A, eIF4B, eIF4G, eIF5B, eIF6, and eIF3H. The term "eukaryotic Initiation Factor (eIF)", as used herein, covers eIF RNA transcripts (RNA transcript variants) such as mRNAs including splice variants of these transcripts and eIF proteins encoded thereby. Thus, the level of the eIFs may be determined by measuring mRNA or protein levels. The term "eukaryotic Initiation Factor (eIF)", as used herein, also covers eIF isoforms. These eIF isoforms are members of a set of highly similar molecules, in particular proteins, that perform the same or similar biological role. For example, eIF4G comprises/encompasses the isoforms eIF4G1, eIF4G2, and/or eIF4G3, encoded by the respective genes. In addition, eIF5A comprises/encompasses the isoforms eIF5A1 and/or eIF5A2, encoded by the respective genes. The level of eIF isoforms may also be determined by measuring mRNA or protein levels. Thus, when it is referred to eIF4G herein, also the isoforms eIF4G1, eIF4G2, and eIF4G3 are meant. In addition, when it is referred to eIF5A herein, also the isoforms eIF5A1 and eIF5A2 are meant.

The term "biological sample", as used herein, refers to any biological sample from an individual or (control) patient comprising at least one of the eIFs claimed herein. The biological sample may be a body fluid sample, e.g. a blood sample or urine sample, or a tissue sample. Biological samples may be mixed or pooled, e.g. a sample may be a mixture of a blood sample and a urine sample. Said biological samples may be provided by removing a body fluid from an individual or (control) patient, but may also be provided by using a previously isolated sample. For example, a blood sample may be taken from an individual or (control) patient by conventional blood collection techniques. The biological sample, e.g. urine sample or blood sample, may be obtained from an individual or (control) patient prior to the initiation of a therapeutic treatment, during the therapeutic treatment, and/or after the therapeutic treatment. If the biological sample, is obtained from at least one (control) patient or healthy (control) individual, e.g. from at least 1, 2, 3, 4, 5, 6, 7, 8, 9, 10, 20, 30, 40, 50, 60, 70, 80, 90, 100, 150, 200, 250, 300, 400, 500, or 1.000 (control) patient(s) or healthy (control) individual(s), it is designated as a "reference biological sample". Preferably, the reference biological sample is from the same source than the biological sample of the individual to be tested, e.g. both are blood samples or urine samples. It is further preferred that both are from the same species, e.g. from a human. It is also (alternatively or additionally) preferred that the measurements of the reference biological sample and the biological sample of the individual to be tested are identical, e.g. both have an identical volume. It is particularly preferred that the reference biological sample and the biological sample are from individuals/(control) patients of the same sex and similar age, e.g. no more than 2 years apart from each other.

The term "body fluid sample", as used herein, refers to any liquid sample derived from the body of an individual or (control) patient containing at least one of the eIFs claimed herein. Said body fluid sample may be a urine sample, blood sample, sputum sample, breast milk sample, cerebrospinal fluid (CSF) sample, cerumen (earwax) sample, gastric juice sample, mucus sample, lymph sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions, e.g. blood fractions, urine fractions or sputum fractions. Body fluid samples may be mixed or pooled. Thus, a body fluid sample may be a mixture of a blood and a urine sample or a mixture of a blood and cerebrospinal fluid sample. Said body fluid sample may be provided by removing a body liquid from an individual or (control) patient, but may also be provided by using previously isolated body fluid sample material. The body fluid sample allows for a non-invasive analysis of an individual. It is further preferred that the body fluid sample has a volume of between 0.01 and 20 ml, more preferably of between 0.1 and 10 ml, even more preferably of between 0.5 and 8 ml, and most preferably of between 1 and 5 ml.

The term "blood sample", as used herein, encompasses a whole blood sample or a blood fraction sample such as a blood serum or blood plasma sample. It is preferred that the blood serum or plasma sample has a volume of between 0.01 and 20 ml, more preferably of between 0.1 and 10 ml, even more preferably of between 0.5 and 8 ml and most preferably of between 1 and 5 ml.

In the context of the present invention, the term "kit of parts (in short: kit)" is understood to be any combination of at least some of the components identified herein, which are combined, coexisting spatially, to a functional unit, and which can contain further components. Said kit may allow point-of-care testing (POCT).

The term "point-of-care testing (POCT)", as used herein, refers to a medical diagnostic testing at or near the point of care that is the time and place of individual care. This contrasts with the historical pattern in which testing was wholly or mostly confined to the medical laboratory, which entailed sending off specimens away from the point of care and then waiting hours or days to learn the results, during which time care must continue without the desired information. Point-of-care tests are simple medical tests that can be performed at the bedside. The driving notion behind POCT is to bring the test conveniently and immediately to the individual to be tested. This increases the likelihood that the individual, physician, and care team will receive the results quicker, which allows for immediate clinical management decisions to be made. POCT is often accomplished through the use of transportable, portable, and handheld instruments and test kits. Small bench analyzers or fixed equipment can also be used when a handheld device is not available—the goal is to collect the specimen and obtain the results in a very short period of time at or near the location of the individual so that the treatment plan can be adjusted as necessary before the individual leaves the hospital.

Embodiments of the Invention

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

The present inventors examined the performance of eukaryotic translation initiation factors (eIFs) in bladder cancer. They ascertained that eIFs represent crossroads in the development of bladder cancer and can serve as biomarkers for bladder cancer. In particular, the present inventors found that eIFs are deregulated between patients suffering from urinary bladder cancer (UBC) and healthy individuals. They identified with eIF1, eIF5A, eIF4B eIF4G, eIF5B, eIF6, and eIF3H new diagnostic biomarkers for UBC.

Thus, in a first aspect, the present invention relates to a (an) (in vitro) method of diagnosing bladder cancer in an individual (suspected of having bladder cancer) comprising the step of: determining the level of at least one eukaryotic Initiation Factor (eIF), e.g. 1, 2, 3, 4, 5, 6, or 7 eIF(s), in a sample from an individual,
wherein the at least one eIF is selected from the group consisting of eIF1, eIF5A, eIF4B eIF4G, eIF5B, eIF6, and eIF3H.

In particular, said individual is suspected of suffering from bladder cancer.

For example, the level(s) of at least 1, at least 2, at least 3, at least 4, at least 5, at least 6, or 7 (all) of the eIFs mentioned above is (are) determined.

Preferred combinations of eIF1, eIF5A, eIF4B eIF4G, eIF5B, and/or eIF6 can be taken from FIG. 10.

It should be noted that eIF4G preferably comprises the isoforms eIF4G1, eIF4G2, and/or eIF4G3. In addition, eIF5A preferably comprises the isoforms eIF5A1 and/or eIF5A2.

In one embodiment, the level of the at least one eIF is compared to a reference level of said at least one eIF (e.g. at least 1, 2, 3, 4, 5, 6 reference level(s), or 7 reference levels). Thus, in one particular embodiment, the present invention relates to a method of diagnosing bladder cancer in an individual (suspected of suffering from pancreatic cancer) comprising the steps of:
(i) determining the level of at least one eukaryotic Initiation Factor (eIF), e.g. 1, 2, 3, 4, 5, 6, or 7 eIF(s), in a biological sample from an individual, and
(ii) comparing the level of the at least one eIF to a reference level of said at least one eIF, wherein the at least one eIF is selected from the group consisting of eIF1, eIF5A, eIF4B eIF4G, eIF5B, eIF6, and eIF3H.

The above comparison allows to diagnose bladder cancer in an individual, in particular in an individual suspected of having bladder cancer. The individual may be diagnosed as suffering from bladder cancer, i.e. being diseased, or as not suffering from bladder cancer, i.e. being healthy.

The reference level may be any level which allows to determine whether an individual suffers from bladder cancer or not. It may be obtained from a (control) subject (i.e. a subject different from the individual to be tested/diagnosed such as a healthy individual) or from the same individual. In the latter case, the individual may be retested for bladder cancer, e.g. in the form of a longitudinal monitoring. It may be determined that the individual is now affected by bladder cancer or still not affected by bladder cancer.

It is preferred that the reference level is the level determined by measuring at least one reference biological sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference biological sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference biological samples from between 2 and 500 healthy individuals. It is even more preferred that the reference level is determined by measuring between 50 and 500 reference biological samples from between 50 and 500 healthy individuals. It is most preferred that the reference level is determined by measuring between 100 and 500 reference biological samples from between 100 and 500 healthy individuals.

It is practicable to take one reference biological sample per individual for analysis. If additional reference biological samples are required, e.g. to determine the reference level in different reference biological samples, the same individual may be (re)tested. Said reference level may be an average reference level. It may be determined by measuring reference levels and calculating the "average" value (e.g. mean, median or modal value) thereof. It is preferred that the reference biological sample is from the same source (e.g. blood sample) than the biological sample isolated from the individual. It is further preferred that the reference level is obtained from a subject of the same gender (e.g. female or male) and/or of a similar age/phase of life (e.g. adults or elderly) than the individual to be tested or diagnosed.

In one preferred embodiment,
the level of the at least one eIF selected from the group consisting of eIF1, eIF5A, and eIF3H (which is) below the reference level indicates that the individual suffers from bladder cancer, and/or
the level of the at least one eIF selected from the group consisting of eIF4B, eIF4G, eIF5B, and eIF6 (which is) above the reference level indicates that the individual suffers from bladder cancer.

In one more preferred embodiment, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below/above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below/above the reference level.

Preferably, the bladder cancer is selected from the group consisting of urothelial bladder cancer (UBC) (also designated as transitional cell bladder cancer), squamous cell bladder cancer, adenocarcinoma, sarcoma, and small cell bladder cancer. More preferably, the bladder cancer is urothelial bladder cancer (UBC). Thus, it is preferred that the first aspect of the present invention relates to a (an) (in vitro) method of diagnosing UBC in an individual (suspected of having UBC) comprising the step of:
determining the level of at least one eukaryotic Initiation Factor (eIF), e.g. 1, 2, 3, 4, 5, 6, or 7 eIF(s), in a sample from an individual,
wherein the at least one eIF is selected from the group consisting of eIF1, eIF5A, eIF4B eIF4G, eIF5B, eIF6, and eIF3H.

In a second aspect, the present invention relates to a (an) (in vitro) method of determining the course of bladder cancer in an individual (suffering from bladder cancer) comprising the step of:
determining the level of at least one eukaryotic Initiation Factor (eIF), e.g. 1, 2, 3, 4, 5, 6, or 7 eIF(s), in a biological sample from an individual,
wherein the at least one eIF is selected from the group consisting of eIF1, eIF5A, eIF4B, eIF4G, eIF5B, eIF6, and eIF3H.

In particular, said individual suffers from bladder cancer.

For example, the level(s) of at least 1, at least 2, at least 3, at least 4, at least 5, at least 6, or 7 (all) of the eIFs mentioned above is (are) determined.

Preferred combinations of eIF1, eIF5A, eIF4B eIF4G, eIF5B, and/or eIF6 can be taken from FIG. 10.

It should be noted that eIF4G preferably comprises the isoforms eIF4G1, eIF4G2, and/or eIF4G3. In addition, eIF5A preferably comprises the isoforms eIF5A1 and/or eIF5A2.

In one embodiment, the level of the at least one eIF is compared to a reference level of said at least one eIF. Thus, in one particular embodiment, the present invention relates to a method of determining the course of bladder cancer in an individual (suffering from bladder cancer) comprising the steps of:
(i) determining the level of at least one eukaryotic Initiation Factor (eIF), e.g. 1, 2, 3, 4, 5, 6, or 7 eIF(s), in a biological sample from an individual,
(ii) comparing the level of the at least one eIF to a reference level of said at least one eIF, wherein the at least one eIF is selected from the group consisting of eIF1, eIF5A, eIF4B, eIF4G, eIF5B, eIF6, and eIF3H.

The above comparison allows to determine the course of bladder cancer in the individual suffering from bladder cancer. It may be determined that bladder cancer worsens in the individual, that bladder cancer does not worsen/is stable in the individual, or that bladder cancer improves in the individual.

The reference level may be any level which allows to determine the course of bladder cancer. It may be obtained from a (control) subject (i.e. a subject different from the individual to be tested such as a healthy individual and/or a patient having bladder cancer) or from the same individual.

Preferably, the reference level is the level determined by measuring at least one reference sample from
at least one healthy individual, and/or
at least one patient having bladder cancer.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals. For example, the level of the at least one eIF selected from the group consisting of eIF1 and eIF5A (which is) below the reference level indicates that the individual (still) suffers from bladder cancer, and/or the level of the at least one eIF selected from the group consisting of eIF4B, eIF4G, eIF5B, and eIF6 (which is) above the reference level indicates that the individual (still) suffers from bladder cancer.

It is further (alternatively or additionally) preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with bladder cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with bladder cancer. It is more preferred that the reference level is the level determined by measuring between 2 and 500 reference samples from between 2 and 500 patients with bladder cancer. It is even more preferred that the reference level is determined by measuring between 50 and 500 reference samples from between 50 and 500 patients with bladder cancer. It is most preferred that the reference level is determined by measuring between 100 and 500 reference samples from between 100 and 500 patients with bladder cancer.

For example,
the level of the at least one eIF selected from the group consisting of eIF1, eIF5A, and eIF3H (which is) comparable with or below the reference level indicates that the individual (still) suffers from bladder cancer, and/or
the level of the at least one eIF selected from the group consisting of eIF4B, eIF4G, eIF5B, and eIF6 (which is) comparable with or above the reference level indicates that the individual (still) suffers from bladder cancer. A level which is comparable with the reference level is preferably identical with the reference level.

More preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below/above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below/above the reference level.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof. It is preferred that the reference biological sample is from the same source (e.g. blood sample) than the biological sample isolated from the individual. It is further preferred that the reference level is obtained from a subject of the same gender (e.g. female or male) and/or of a similar age/phase of life (e.g. adults or elderly) than the individual to be tested or diagnosed.

In one alternative or additional embodiment, said determining comprises determining the level of the at least one eIF in a biological sample (from an individual) at a first point in time and in at least one further biological sample (from the (same) individual) at a later point in time and comparing said levels determined at the different time points.

Thus, in one particular embodiment, the present invention relates to a method of determining the course of bladder cancer in an individual (suffering from bladder cancer) comprising the steps of:
(i) determining the level of at least one eIF, e.g. 1, 2, 3, 4, 5, 6, or 7 eIF(s), in a biological sample from an individual (suffering from bladder cancer) at a first point in time and in at least one further biological sample from the (same) individual at a later point in time, and
(ii) comparing said levels determined at the different time points,
wherein the at least one eIF is selected from the group consisting of eIF1, eIF5A, eIF4B, eIF4G, eIF5B, eIF6, and eIF3H.

This proceeding allows to determine the course of bladder cancer in an individual suffering from bladder cancer over an extended period of time, such as months or years, e.g. 1, 2, 3, 4, 5, 6, 7, 8, 9, 10, or 11 month(s), 1, 2, 3, 4, or 5 year(s).

It is preferred that the level of the at least one eIF selected from the group consisting of eIF1, eIF5A, and eIF3H which
(i) decreases over time indicates that bladder cancer worsens in the individual,
(ii) does not change over time indicates that bladder cancer does not worsen/is stable in the individual, or
(iii) increases over time indicates that bladder cancer improves in the individual.

It is also preferred that the level of the at least one eIF selected from the group consisting of eIF4B, eIF4G, eIF5B, and eIF6 which
(i) increases over time indicates that bladder cancer worsens in the individual,
(ii) does not change over time indicates that bladder cancer does not worsen/is stable in the individual, or
(iii) decreases over time indicates that bladder cancer improves in the individual.

The increase may be at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold over time.

The decrease may be at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold over time.

"Stable", as mentioned above, means that the level varies over time between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected level variation is within the accuracy of a measurement. The accuracy of a measurement depends on the measurement method used. Preferably, the level is constant over time.

The time period between the first point in time and the later point(s) in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 24 months (2 years), at least 3 years, at least 4 years, at least 5 years, at least 6 years, at least 7 years, at least 8 years, at least 9 years, or at least 10 years. For example, the individual may be routinely checked, e.g. once or twice a year. The individual may be (re)tested at 2, 3, 4, 5, 6 7, 8, 9, or 10 time points (first point in time and further point(s) in time).

In addition to the determination of the course of bladder cancer, the treatment of this disease can be monitored. In particular, the individual receives, has received, or had received a treatment, in particular a therapeutic treatment, of bladder cancer during the determination of the course of bladder cancer.

It is more preferred that
(i) the level of the at least one eIF selected from the group consisting of eIF1, eIF5A, and eIF3H which increases over time indicates that the individual responds to said treatment,
(ii) the level of the at least one eIF selected from the group consisting of eIF1, eIF5A, and eIF3H which does not change over time indicates that the individual does not respond/does not respond sufficiently to said treatment, or
(iii) level of the at least one eIF selected from the group consisting of eIF1, eIF5A, and eIF3H which decreases over time indicates that the individual does not respond to said treatment. It is also more preferred that
(i) the level of the at least one eIF selected from the group consisting of eIF4B, eIF4G, eIF5B, and eIF6 which decreases over time indicates that the individual responds to said treatment,
(ii) the level of the at least one eIF selected from the group consisting of eIF4B, eIF4G, eIF5B, and eIF6 which does not change over time indicates that the individual does not respond/does not respond sufficiently to said treatment, or
(iii) level of the at least one eIF selected from the group consisting of eIF4B, eIF4G, eIF5B, and eIF6 which increases over time indicates that the individual does not respond to said treatment.

A treatment response which is not sufficient is a response which does not improve the health status of the individual.

The therapeutic treatment of bladder cancer is preferably selected from the group consisting of the administration of a drug, surgery, chemotherapy, radiotherapy, and a combination thereof. The individual may receive a treatment during the complete determination/monitoring process (e.g. the administration of a drug) or may receive a treatment before, at, or after a first point in time (e.g. the administration of a drug) and may be retested at a later point in time. In particular, said first point in time may be before the initiation of a treatment and said later point in time may be during the treatment and/or after the treatment. If the treatment encompasses the administration of a drug and the individual responds to said treatment, the drug administration may be continued, the dose of the drug may be reduced, or the drug administration may be stopped. If the treatment encompasses the administration of a drug and the individual does not respond to said treatment, the dose of the drug may be increased, the drug may be changed, or the therapy mode may be changed, e.g. from drug administration to surgery or radiotherapy.

Preferably, the bladder cancer is selected from the group consisting of urothelial bladder cancer (UBC) (also designated as transitional cell bladder cancer), squamous cell bladder cancer, adenocarcinoma, sarcoma, and small cell bladder cancer. More preferably, the bladder cancer is urothelial bladder cancer (UBC). Thus, it is preferred that the second aspect of the present invention relates to a (an) (in vitro) method of determining the course of UBC in an individual (suffering from UBC) comprising the step of: determining the level of at least one eukaryotic Initiation Factor (eIF), e.g. 1, 2, 3, 4, 5, 6, or 7 eIF(s), in a biological sample from an individual, wherein the at least one eIF is selected from the group consisting of eIF1, eIF5A, eIF4B, eIF4G, eIF5B, eIF6, and eIF3H.

In the methods of the first and second aspect of the present invention, it is preferred that the biological sample is a tissue sample, e.g. tumor tissue sample, or a body fluid sample. It is also preferred that the reference biological sample is a tissue sample, e.g. tumor tissue sample, or a body fluid sample. Preferably, the body fluid sample is selected from the group consisting of a blood sample, an urine sample, a lymph sample, a saliva sample and a combination thereof. More preferably, the blood sample is a whole blood sample or a blood fraction sample. Even more preferably, the blood fraction sample is a blood serum sample or a blood plasma sample.

Preferably, the aforementioned samples are pre-treated before they are used in the methods of the first and second aspect of the present invention. Said pre-treatment may include treatments required to separate the at least one eIF described herein, or to remove excessive material or waste. Furthermore, pre-treatments may aim at sterilizing samples and/or removing contaminants such as undesired cells, bacteria or viruses. Suitable techniques comprise centrifugation, extraction, fractioning, ultrafiltration, protein precipitation followed by filtration and purification and/or enrichment of compounds. Moreover, other pre-treatments are carried out in order to provide the at least one eIF described herein in a form or concentration suitable for analysis.

In one preferred embodiment of the methods of the first and second aspect of the present invention, the biological sample used to determine the level of the at least one eIF is a tissue sample, e.g. tumor tissue sample (obtainable e.g. by biopsy) or a body fluid sample. The eIF markers of the present invention can be found in the tissue affected with the tumor and in body fluids like blood and blood components (e.g. plasma or serum).

According to another preferred embodiment of the methods of the first and second aspect of the present invention, the level of the at least one eIF is determined by measuring mRNA or protein levels. The levels of the eIFs in the methods of the first and second aspect of the present invention can be determined either by measuring mRNA molecules encoding said eIFs or the eIFs as such in form of proteins. Methods to determine mRNA levels and protein levels in a sample are well known. mRNA expression levels are usually measured by polymerase chain reaction (PCR), in particular by reverse transcription quantitative polymerase chain reaction (RT-PCR and qPCR) or real-time PCR. RT-PCR is used to create a cDNA from the mRNA. The cDNA may be used in a qPCR assay to produce fluorescence as the DNA amplification process progresses. This fluorescence is proportional to the original mRNA amount in the samples. Other methods to be used include Northern blots, Fluorescence in situ hybridization (FISH), microarrays, and RT-PCR combined with capillary electrophoresis. Protein levels of eIFs are preferably determined using immunoassays. Such methods are based on the binding of an antibody, a derivative or a fragment thereof to its corresponding target (i.e. eIF). Polyclonal and monoclonal antibodies can be used in such methods. Derivatives or fragments of antibodies include Fab fragments, F(ab')$_2$ fragments, Fv fragments, single chain antibodies and single domain antibodies. Preferred immunoassays include Western blot, Immunohistochemistry, ELISA (enzyme-linked immunosorbent assay), radioimmunoassays, fluorescence resonance energy transfer (FRET) or time resolved-FRET (TR-FRET). It is particularly preferred to use antibodies and derivatives or fragments of antibodies which have been obtained from a non-human source. These antigen binding molecules can be of porcine, rabbit, murine, camel or rat origin. Of course, it is also possible to use antibodies and derivatives or fragments thereof which are recombinantly produced in plants or cell cultures, in particular microbial cell cultures (e.g. bacteria, yeast).

In a third aspect, the present invention relates to the (in vitro) use of at least one eIF, e.g. 1, 2, 3, 4, 5, 6, or 7 eIF(s), for diagnosing bladder cancer in an individual (suspected of having bladder cancer) or determining the course of bladder cancer in an individual (suffering from bladder cancer), wherein the at least one eIF is selected from the group consisting of eIF1, eIF5A, eIF4B, eIF4G, eIF5B, eIF6, and eIF3H.

For example, at least 1, at least 2, at least 3, at least 4, at least 5, at least 6, or 7 (all) of the eIFs mentioned above is (are) used.

Preferred combinations of eIF1, eIF5A, eIF4B eIF4G, eIF5B, and/or eIF6 can be taken from FIG. 10.

It should be noted that eIF4G preferably comprises the isoforms eIF4G1, eIF4G2, and/or eIF4G3. In addition, eIF5A preferably comprises the isoforms eIF5A1 and/or eIF5A2.

For the above mentioned use, the level of the above mentioned eIFs is determined in a biological sample from an individual to be tested. It is preferred that the biological sample is a tissue sample, e.g. tumor tissue sample, or body fluid sample. Preferably, the body fluid sample is selected from the group consisting of a blood sample, a urine sample, and a combination thereof. More preferably, the blood sample is a whole blood sample or a blood fraction sample. Even more preferably, the blood fraction sample is a blood serum sample or a blood plasma sample.

Preferably, the bladder cancer is selected from the group consisting of urothelial bladder cancer (also designated as transitional cell bladder cancer), squamous cell bladder cancer, adenocarcinoma, sarcoma, and small cell bladder cancer. More preferably, the bladder cancer is urothelial bladder cancer.

As to further preferred embodiments, it is referred to the first and second aspect of the present invention.

In a fourth aspect, the present invention relates to (the use of) a kit for diagnosing bladder cancer in an individual (suspected of having bladder cancer) or determining the course of bladder cancer in an individual (suffering from bladder cancer) comprising means for determining the level of at least one eIF, e.g. 1, 2, 3, 4, 5, 6, or 7 eIF(s), in a biological sample from an individual, wherein the at least one eIF is selected from the group consisting of eIF1, eIF5A, eIF4B, eIF4G, eIF5B, eIF6, and eIF3H.

Preferably, the kit is used in vitro.

For example, the means are for determining the level of at least 1, at least 2, at least 3, at least 4, at least 5, at least 6, or 7 (all) of the eIFs mentioned above.

Preferred combinations of eIF1, eIF5A, eIF4B eIF4G, eIF5B, and/or eIF6 can be taken from FIG. 10.

It should be noted that eIF4G preferably comprises the isoforms eIF4G1, eIF4G2, and/or eIF4G3. In addition, eIF5A preferably comprises the isoforms eIF5A1 and/or eIF5A2.

Said means may be primers or primer pairs allowing the detecting of the above mentioned eIFs on the RNA transcript, e.g. mRNA, level and/or antibodies, antibody derivatives or fragments of antibodies allowing the detection of the above mentioned eIFs on the protein level.

In addition, said means encompass dipstrips or dipsticks, e.g. urine or blood dipstrips or dipsticks. Said means are tools used to determine changes in individual's urine or blood. A dipstrip or dipstick comprises different chemical pads or reagents which react (e.g. change color, in particular by applying an immune assay) when immersed in (e.g. blood or urine), and then removed from the biological sample (e.g. urine or blood sample). The result can be read after a few minutes, preferably after a few seconds.

It is preferred that the kit is useful for conducting the methods of the first and second aspect of the present invention.

It is further preferred that the kit comprises
(i) a container, and/or
(ii) a data carrier.

Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise a reference level of the at least one eIF referred to herein. In case that the data carrier comprises an access code which allows the access to a database, said reference level is deposited in this database. In addition, the data carrier may comprise information or instructions on how to carry out the methods of the first and second aspect of the present invention.

Said kit may also comprise materials desirable from a commercial and user standpoint including a buffer(s), a reagent(s) and/or a diluent(s) for determining the level mentioned above.

Preferably, the bladder cancer is selected from the group consisting of urothelial bladder cancer (also designated as transitional cell bladder cancer), squamous cell bladder cancer, adenocarcinoma, sarcoma, and small cell bladder cancer. More preferably, the bladder cancer is urothelial bladder cancer.

As to further preferred embodiments, it is referred to the first and second aspect of the present invention.

The individual tested in the methods of the first and second aspect of the present invention and referred to in the third and fourth aspect of the present invention may be a mammal. Preferably, the mammal is a human.

The present invention is summarized as follows:

1. A method of diagnosing bladder cancer in an individual (suspected of having bladder cancer) comprising the step of:
    determining the level of at least one eukaryotic Initiation Factor (eIF) in a biological sample from an individual, wherein the at least one eIF is selected from the group consisting of eIF1, eIF5A, eIF4B, eIF4G, eIF5B, eIF6, and eIF3H.
2. The method of item 1, wherein the level of the at least one eIF is compared to a reference level of said at least one eIF.
3. The method of item 2, wherein the reference level is the level determined by measuring at least one reference biological sample from at least one healthy individual.
4. The method of items 2 or 3, wherein
    the level of the at least one eIF selected from the group consisting of eIF1, eIF5A, and eIF3H which is below the reference level indicates that the individual suffers from bladder cancer, and/or
    the level of the at least one eIF selected from the group consisting of eIF4B, eIF4G, eIF5B, and eIF6 which is above the reference level indicates that the individual suffers from bladder cancer.
5. A method of determining the course of bladder cancer in an individual (suffering from bladder cancer) comprising the step of:
    determining the level of at least one eukaryotic Initiation Factor (eIF) in a biological sample from an individual, wherein the at least one eIF is selected from the group consisting of eIF1, eIF5A, eIF4B, eIF4G, eIF5B, eIF6, and eIF3H.
6. The method of item 5, wherein the level of the at least one eIF is compared to a reference level of said at least one eIF.
7. The method of item 6, wherein the reference level is the level determined by measuring at least one reference biological sample from
    at least one healthy individual, or
    at least one patient having bladder cancer.
8. The method of any one of items 5 to 7, wherein said determining comprises determining the level of the at least one eIF in a biological sample at a first point in time and in at least one further biological sample at a later point in time and comparing said levels determined at the different time points.
9. The method of item 8, wherein the level of the at least one eIF selected from the group consisting of eIF1, eIF5A, and eIF3H which
    (i) decreases over time indicates that bladder cancer worsens in the individual,
    (ii) does not change over time indicates that bladder cancer does not worsen/is stable in the individual, or
    (iii) increases over time indicates that bladder cancer improves in the individual.
10. The method of items 8 or 9, wherein the level of the at least one eIF selected from the group consisting of eIF4B, eIF4G, eIF5B, and eIF6 which
    (i) increases over time indicates that bladder cancer worsens in the individual,
    (ii) does not change over time indicates that bladder cancer does not worsen/is stable in the individual, or
    (iii) decreases over time indicates that bladder cancer improves in the individual.
11. The method of any one of items 5 to 10, wherein the individual receives, has received, or had received a therapeutic treatment of bladder cancer.
12. The method of item 11, wherein
    (i) the level of the at least one eIF selected from the group consisting of eIF1, eIF5A, and eIF3H which increases over time indicates that the individual responds to said treatment,
    (ii) the level of the at least one eIF selected from the group consisting of eIF1, eIF5A, and eIF3H which does not change over time indicates that the individual does not respond to said treatment, or (iii) level of the at least one eIF selected from the group consisting of eIF1, eIF5A, and eIF3H which decreases over time indicates that the individual does not respond to said treatment.

13. The method of items 11 or 12, wherein
   (i) the level of the at least one eIF selected from the group consisting of eIF4B, eIF4G, eIF5B, and eIF6 which decreases over time indicates that the individual responds to said treatment,
   (ii) the level of the at least one eIF selected from the group consisting of eIF4B, eIF4G, eIF5B, and eIF6 which does not change over time indicates that the individual does not respond to said treatment, or
   (iii) level of the at least one eIF selected from the group consisting of eIF4B, eIF4G, eIF5B, and eIF6 which increases over time indicates that the individual does not respond to said treatment.

14. The method of any one of items 11 to 13, wherein the therapeutic treatment of bladder cancer is selected from the group consisting of the administration of a drug, surgery, chemotherapy, radiotherapy, and a combination thereof.

15. The method of any one of items 1 to 14, wherein the bladder cancer is selected from the group consisting of urothelial bladder cancer (also designated as transitional cell bladder cancer), squamous cell bladder cancer, adenocarcinoma, sarcoma, and small cell bladder cancer.

16. The method of any one of items 1 to 15, wherein the biological sample is a tissue sample or a body fluid sample.

17. The method of item 16, wherein the body fluid is blood, lymph, or saliva.

18. The method of item 17, wherein the blood is whole blood or a blood fraction, preferably serum, plasma, or blood cells.

19. The method of any one of items 1 to 18, wherein the level of the at least one eIF is determined by measuring mRNA or protein levels.

20. Use of at least one eIF for diagnosing bladder cancer in an individual (suspected of having bladder cancer) or determining the course of bladder cancer in an individual (suffering from bladder cancer),
   wherein the at least one eIF is selected from the group consisting of eIF1, eIF5A, eIF4B, eIF4G, eIF5B, eIF6, and eIF3H.

21. A kit for diagnosing bladder cancer in an individual (suspected of having bladder cancer) or determining the course of bladder cancer in an individual (suffering from bladder cancer) comprising
   means for determining the level of at least one eIF in a biological sample from an individual, wherein the at least one eIF is selected from the group consisting of eIF1, eIF5A, eIF4B, eIF4G, eIF5B, eIF6, and eIF3H.

22. The kit of item 21, wherein the kit is useful for conducting the methods according to any one of items 1 to 19.

23. The kit of items 21 or 22, wherein the kit further comprises
   (i) a container, and/or
   (ii) a data carrier.

24. The kit of item 23, wherein the data carrier comprises instructions on how to carry out the methods according to any one of items 1 to 19.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

FISG. 3A-3B: TMA-Blocks containing patient sample after construction. FIG. 3A) The blocks in this row contain the tumor tissue to be analyzed and the diameter of a tissue cylinder is 0.6 mm. The distance between two cylinders is 1.7 mm A 6×13 coordinate grid was used as template. Three tumor tissue cylinders were embedded per patient (107 patients, tumor group). This results in 321 tissue cylinders in total. FIG. 3B) The cylinders contain the urothelial tissue to be analyzed. Here the diameter of a cylinder is sized with 1.0 mm larger in comparison to 0.6 mm for the tumor tissue. The distance between two cylinders is 2.5 mm. Two urothelial tissue cylinders were embedded per patient (76 patients, comparison group). This results in 152 embedded urothelial tissue cylinders.

FIGS. 4A-4C: Evaluation of the immunohistochemical staining for eIF1. FIG. 4A) NPar Tests, Descriptive statistics, FIG. 4B) Outcome of the immunohistochemical staining, left graphic=cancerous tissue, right graphic=normal tissue, FIG. 4C) Wilcoxon Signed Rank Tests, test statistics.

FIGS. 5A-5C: Evaluation of the immunohistochemical staining for eIF4B. FIG. 5A) NPar Tests, Descriptive statistics, FIG. 5B) Outcome of the immunohistochemical staining, left graphic=cancerous tissue, right graphic=normal tissue, FIG. 5C) Wilcoxon Signed Rank Tests, test statistics.

FIGS. 6A-6C: Evaluation of the immunohistochemical staining for eIF4G. FIG. 6A) NPar Tests, Descriptive statistics, FIG. 6B) Outcome of the immunohistochemical staining, left graphic=cancerous tissue, right graphic=normal tissue, FIG. 6C) Wilcoxon Signed Rank Tests, test statistics.

FIGS. 7A-7C: Evaluation of the immunohistochemical staining for eIF5A. FIG. 7A) NPar Tests, Descriptive statistics, FIG. 7B) Outcome of the immunohistochemical staining, left graphic=cancerous tissue, right graphic=normal tissue, FIG. 7C) Wilcoxon Signed Rank Tests, test statistics.

FIGS. 8A-8C: Evaluation of the immunohistochemical staining for eIF5B. FIG. 8A) NPar Tests, Descriptive statistics, FIG. 8B) Outcome of the immunohistochemical staining, left graphic=cancerous tissue, right graphic=normal tissue, FIG. 8C) Wilcoxon Signed Rank Tests, test statistics.

FIGS. 9A-9C: Evaluation of the immunohistochemical staining for eIF6. FIG. 9A) NPar Tests, Descriptive statistics, FIG. 9B) Outcome of the immunohistochemical staining, left graphic=cancerous tissue, right graphic=normal tissue, FIG. 9C) Wilcoxon Signed Rank Tests, test statistics.

FIG. 10: Preferred eIF combinations of eIF1, eIF5A, eIF4B eIF4G, eIF5B, and/or eIF6.

EXAMPLES

The examples given below are for illustrative purposes only and do not limit the invention described above in any way.

Material and Methods

1. Patient Samples

The study comprised 107 patients with the diagnosis UBC which underwent a TUR-B treatment or radical cystectomy. Tumor material was obtained from the department of Pathology at the Medical University of Magdeburg. Patients who were diagnosed with urothelial bladder cancer (UBC) were considered as suitable for the project. 107 formalin-fixed, paraffin-embedded patient samples were retrospectively collected from the University Hospital in Magdeburg. Hematoxylin-eosin-stained (H/E) slides were reviewed by two experienced, board-certified pathologist, who confirmed the diagnoses and identified the areas of tumor and non-neoplastic tissue for each tissue microarray core. 107 of the 107 patient samples contained tumor tissue and were considered as suitable for the manufacturing of a Tumor-TMA (tumor group). 76 of the 107 patient samples contained non-neoplastic urothelial tissue and were used to manufacture a Non-Tumor-TMA (comparison group).

Clinical patient data was stored in a Microsoft Excel 2016 table. The following data was determined: Forename, family name, sex, date of birth, case number, time of first diagnosis, histopathological diagnosis of tumor tissue, t-stage, tumor-grade.

2. Tissue Microarray (TMAs)

Tissue Microarrays (TMAs) are a unique method which allows to embed over 1000 tissue cores in a paraffin block. This technique gives opportunity to perform immunohistochemistry and analyze specified regions of various tumors.

3. Establishing the Arraying Technique

Figure 1:
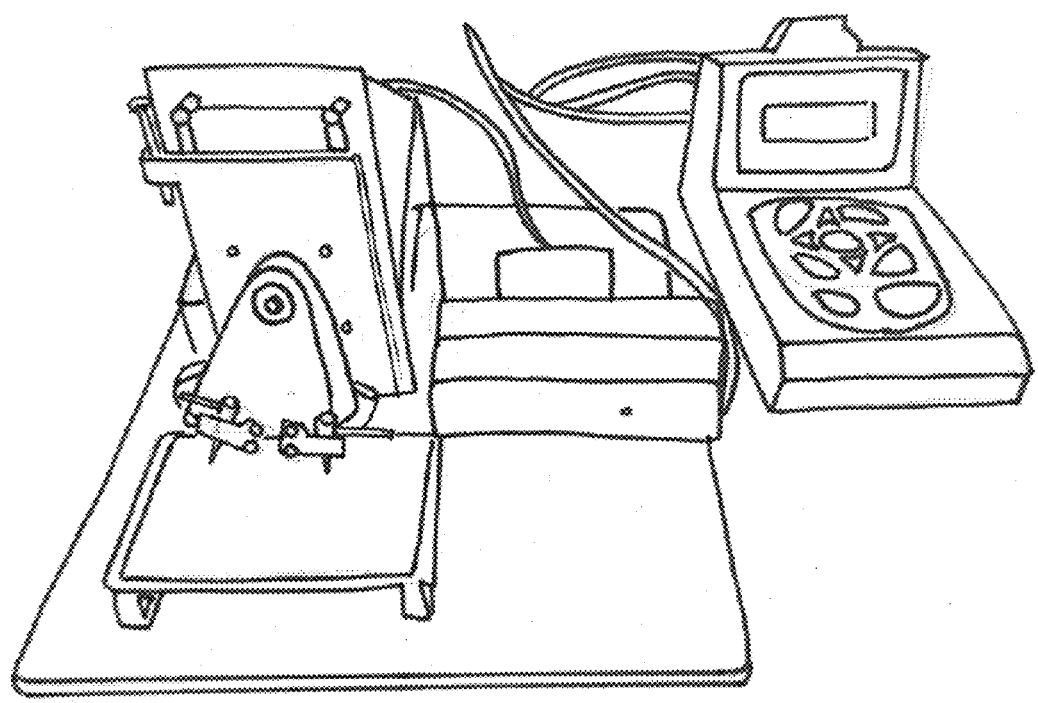
FIG. 1: Manual production of a Tissue Microarray-Block (TMA-Block). 1) The Acceptor-Tube (left) is used to punch out paraffin of a pre-selected region of the recipient TMA-Block. 2) The Donor-Tube (right) is used to punch out a pre-selected region of a donor block with tumor tissue. 3) The tissue core is transferred into the pre-made hole of the recipient block.
Figure 2:
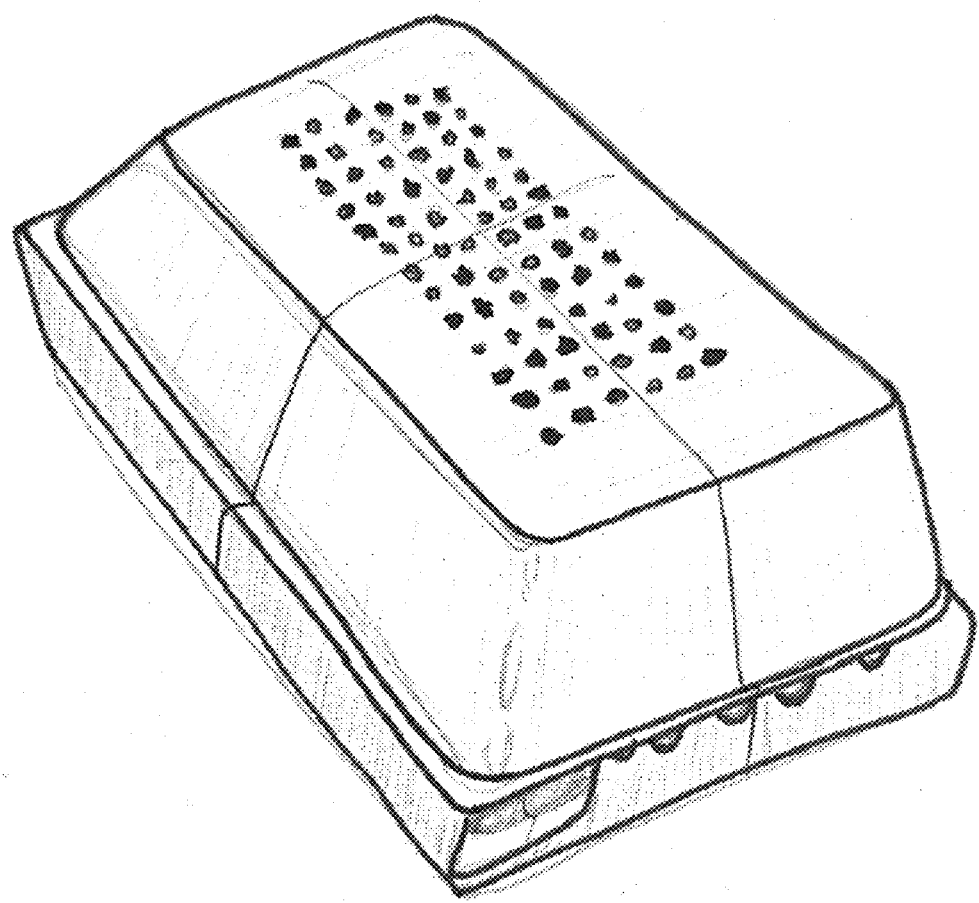
FIG. 2: Tissue microarray (TMA). Tissue cores of 0.6 mm in diameter were punched out from the chosen tumor areas and embedded as TMA in a fresh paraffin block according to a specific 6×13 pattern. The distance between two cores is 1.7 mm. This specific coordinate system was established internally and showed the best results.
Figure 4B:
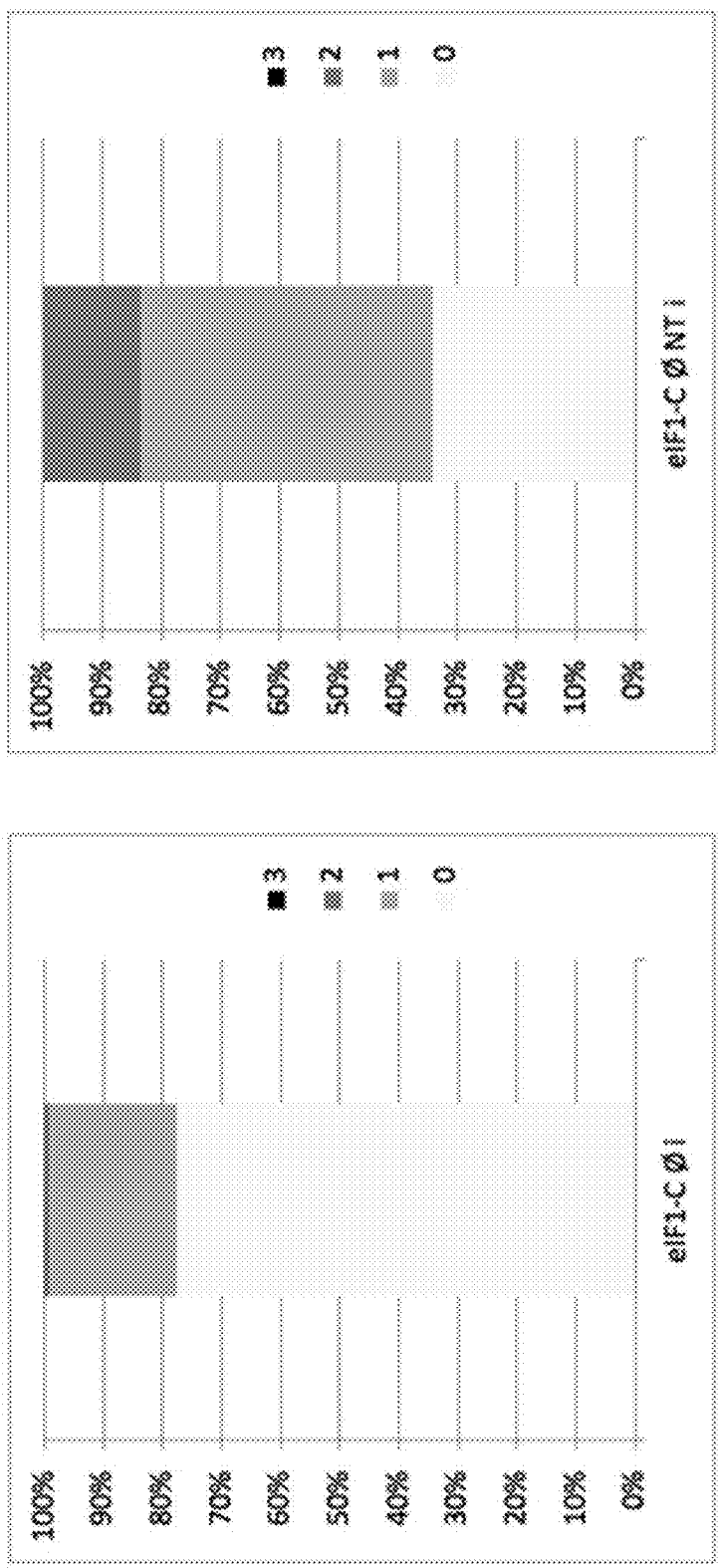
Figure 5B:
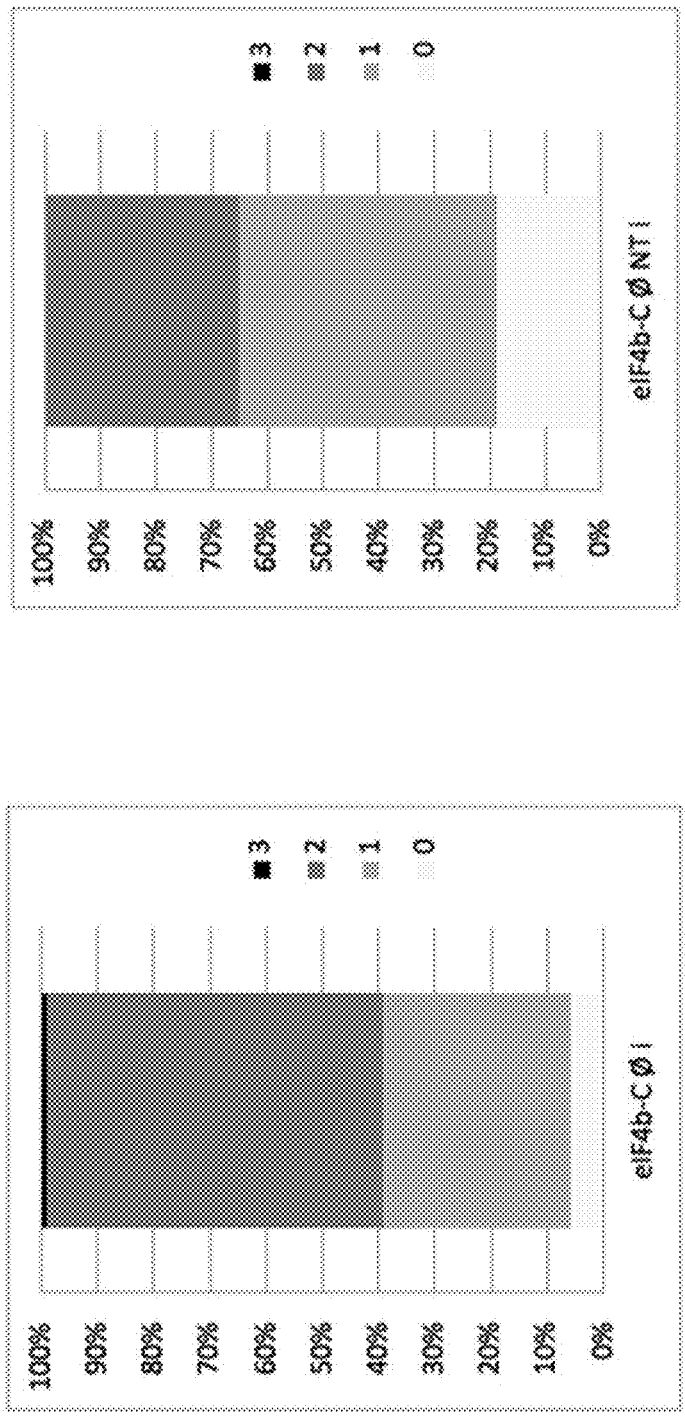
Figure 6B:
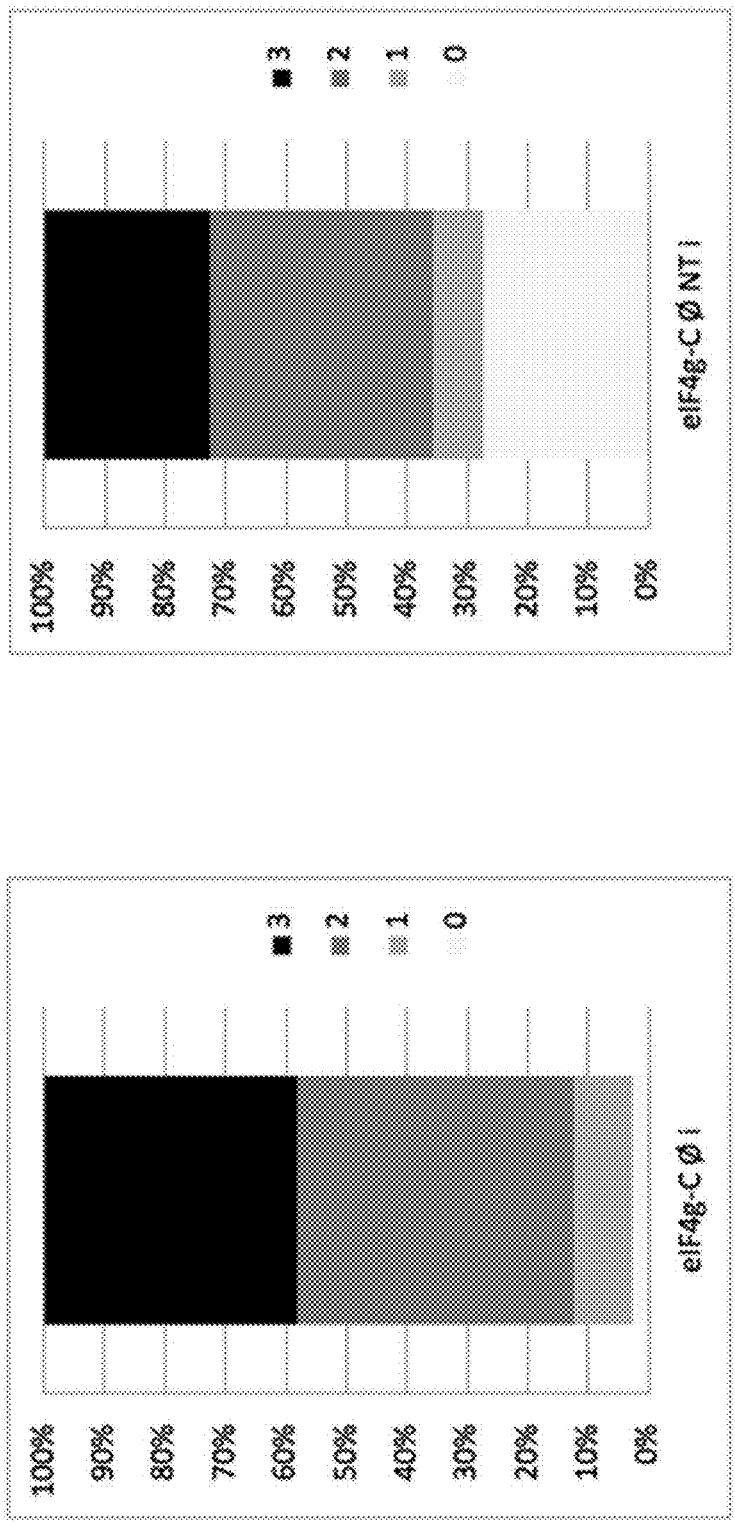
Figure 7B:
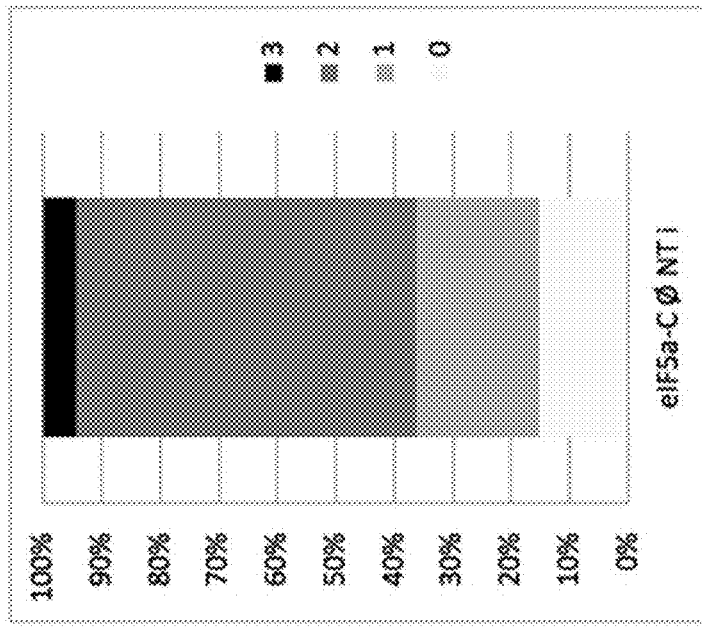
Figure 7B:
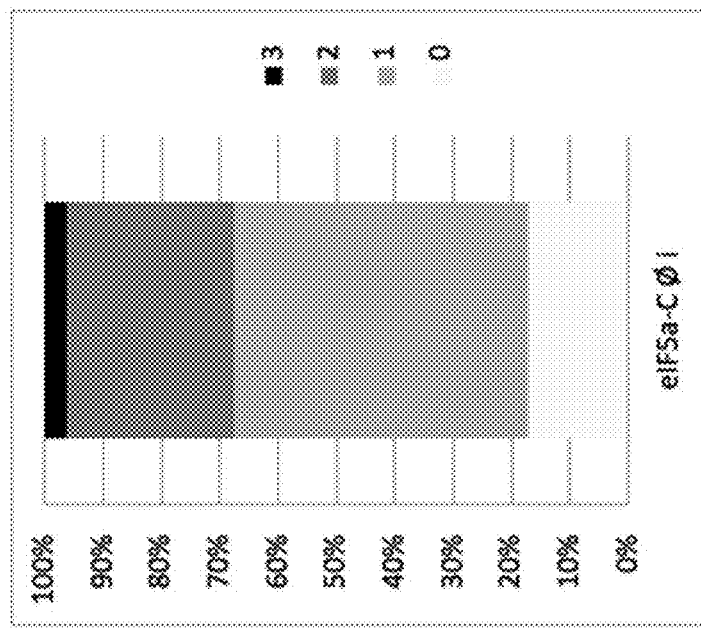
Figure 8B:
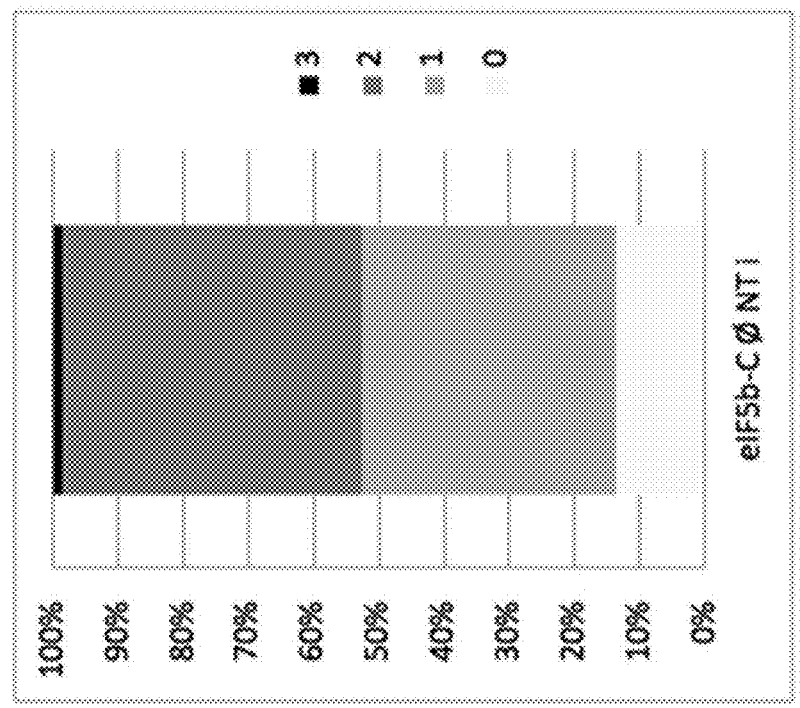
Figure 8B:
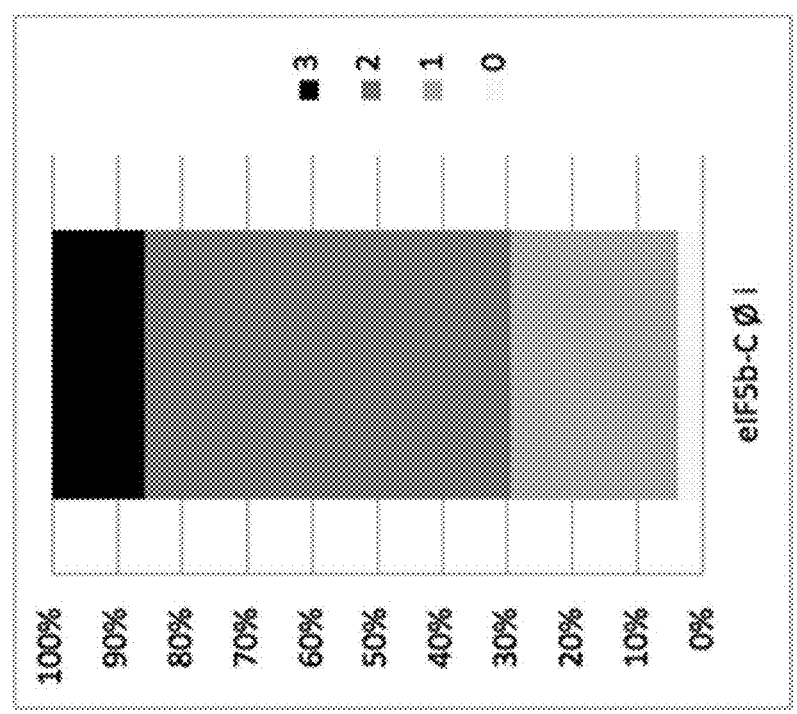
Figure 9B:
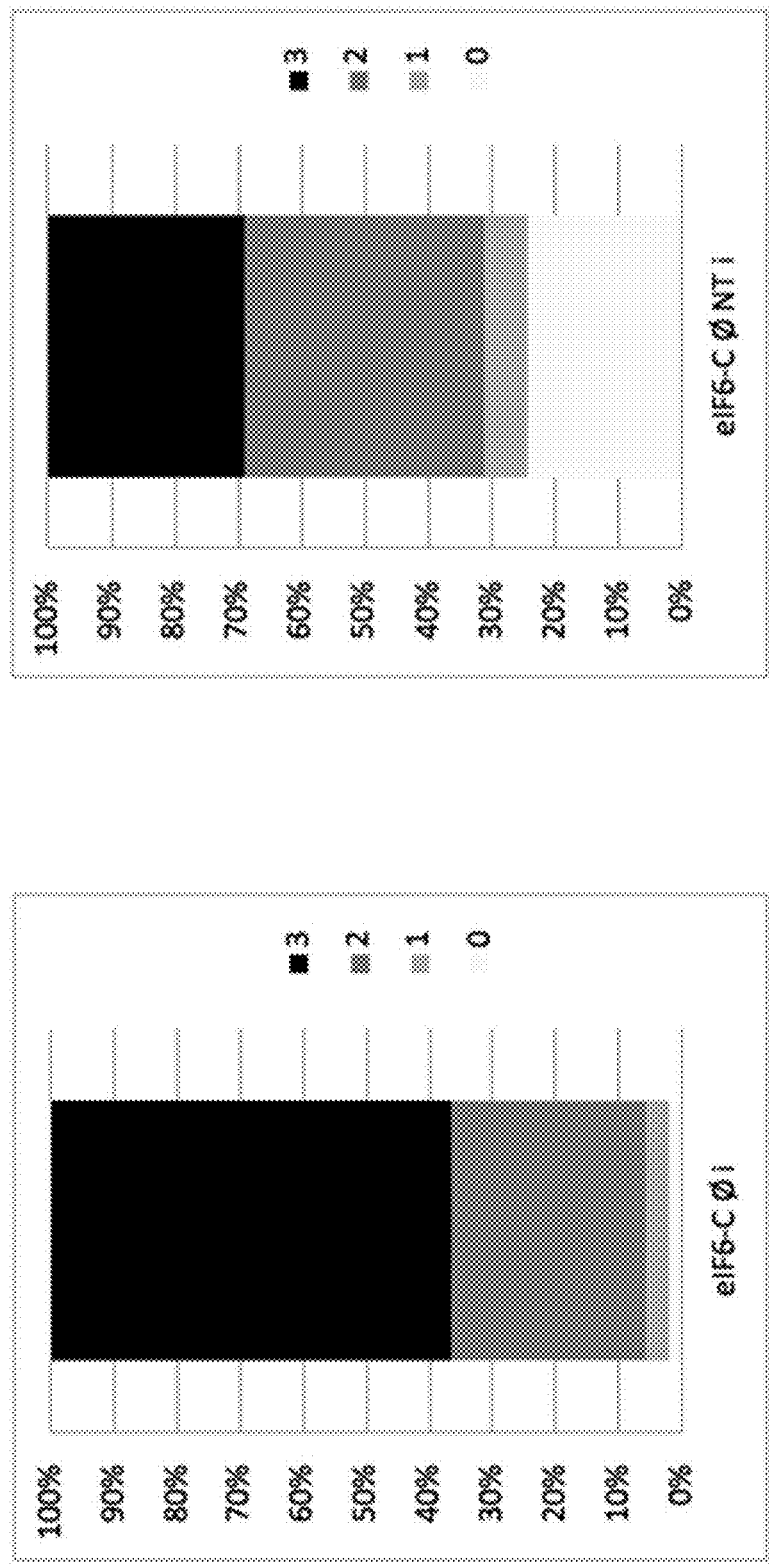

For the Production of the TMAs a Manual-Tissue-Arraying Instrument (MTA Booster, Version 01, Alphelys, France) was used. The manual production of a TMA-block is described in FIG. 1. A tissue microarray is shown in FIG. 2.

4. TMAs with UBC Samples

To prepare for the cut, the MIAs were placed in a warming cabinet for four hours (40° C.). The TMAs were cut into 4 μm thick slices. After smoothing in a water bath, the sections were transferred to Polysine Slides® Adhesion Slide (Thermo Scientific). 12 cuts were made per TMA (9 TMAs× 12 cuts=108), In the next step, the immunohistochemical staining took place. FIG. 3 shows the TMA-blocks containing patient sample after construction.

5. Immunohistochemical Staining

The protein expression of eIF1, eIF1AY, eIF2A, eIF3A, eIF3B, eIF3H, eIF4B, eIF4E, eIF4G, eIF5A, eIF5B, eIF6 was analyzed by immunohistochemical staining. The staining was carried out under standardized conditions in the BenchMark® Ultra stainer (Ventana Medical Systems, Tucsin, USA). For antigen unmasking, sections were treated with Cell Conditioning Solution® (CC1-mild, Ventana). The incubation time per primary antibody used was 32 minutes. The detailed information on the antibodies, manufacturer names and established dilutions can be found in Table 1.

TABLE 1

Detailed overview of the antibodies that were used for IHC

| antibody | manufacturer | order-Nr. | established dilution | method |
|---|---|---|---|---|
| eIF1 Monocl. AB (2B9) | Thermo Fischer | MA1-077 | 1:3000 CC1mild | DAB BenchmarkUltra |
| eIF1AY | Thermo Fisher (Invitrogen) | PA5-31198 | 1:500 CC1mild | DAB BenchmarkUltra |
| eIF2α (D7D3) XP | Cell Signalling | #5324P | 1:2000 CC1mild | DAB BenchmarkUltra |
| eIF3A | Thermo Fisher (Invitrogen) | PA5-31296 | 1:100 CC1mild | DAB BenchmarkUltra |
| eIF3B (eIF3η D-9) | Santa Cruz | sc-137215 | 1:50 CC1mild | DAB BenchmarkUltra |
| eIF3H (D9C1) XP | Cell Signalling | #3413 | 1:1600 CC1mild | DAB BenchmarkUltra |
| eIF4B | GeneTex | GTX33175 | 1:500 CC1mild | DAB BenchmarkUltra |
| eIF4E | Cell Signalling | #9742 | 1:100 CC1mild | DAB BenchmarkUltra |
| eIF4G | Cell Signalling | #2498 | 1:50 CC1mild | DAB BenchmarkUltra |
| eIF5A | Thermo Fisher (Invitrogen) | PA5-29204 | 1:250 CC1mild | DAB BenchmarkUltra |
| eIF5B | Thermo Fisher (Invitrogen) | PA5-36456 | 1:50 CC1mild | DAB BenchmarkUltra |
| eIF6 | biomol/BETHYL | A303-030A/M | 1:100 CC1mild | DAB BenchmarkUltra |

6. Evaluation of the Immunohistochemical Staining

The 108 TMA sequences were scanned in a NanoZoomer 360S Whole Slide Imaging Scanner (Hamamatsu). The evaluation was done semiquantitatively using the digital pathology program NanoZoomerDigitalPathology (NDP.View2).

In the evaluation, the staining intensity I (Intensity=0-3) and the percentage of the stained tumor area D (Density=0-100%) were separately analyzed for each spot and the medians were formed. It was also differentiated per spot whether it was a cytoplasmic, nuclear or mixed cytoplasmic-nuclear staining.

The following values were used for the intensity I of the staining:

0—negative color reaction

1—slightly positive staining

2—medium positive staining

3—strong positive staining

The median of staining intensity I (min 0-max 3) was then multiplied by the median of the percentage of stained area D (min 0-max 100). The product was then divided by 10 to obtain the immunoreactive score (IRS score: min 0-max 30) per patient case. Both staining intensity and IRS score formed the basis for further statistical data processing.

$$IRS = \frac{I * D}{10}$$

7. Statistical Analysis

The statistical evaluation was carried out using the Microsoft Excel program. The data was then exported to IBM SPSS Statistics (version 22) and statistically evaluated. Differences in eIF expression between tumor and non-tumor groups were assessed using Wilcoxon non-parametric test. A p value <0.05 was considered as statistically significant. Statistical analysis was performed with the statistic program IBM® SPSS® Statistics Version 22. Graph generation was performed using Microsoft Word and Excel.

Results

In this study, the performance of eukaryotic translation initiation factors (eIFs) in bladder cancer was examined. It was found that eIFs are deregulated between patients suffering from UBC and healthy individuals. With eIF1, eIF5A, eIF4B eIF4G, eIF5B, eIF6, and eIF3H seven new diagnostic biomarkers for UBC were identified. These new diagnostic biomarkers allow the diagnosis and monitoring of UBC. In particular, immunohistochemical data from tissue microarray (n=107) demonstrated significantly higher expression levels of eIF4B eIF4G, eIF5B, and eIF6 in patients suffering from UBC compared to non-neoplastic tissue (healthy controls). In contrast thereto, eIF1 and eIF5A were significantly downregulated in patients suffering from UBC compared to non-neoplastic tissue (healthy controls). The results are shown in FIGS. 4 to 9. eIF3H was also downregulated in patients suffering from UBC compared to non-neoplastic tissue (healthy controls). FIG. 10 lists preferred eIF combinations of eIF1, eIF5A, eIF4B eIF4G, eIF5B, and/or eIF6.

The invention claimed is:

1. A method for treating bladder cancer, comprising the steps of:
   (i) providing a bladder tissue sample from an individual suspected of suffering from bladder cancer;
   (ii) determining the level of eIF4B in the bladder tissue sample;
   (iii) diagnosing the individual as suffering from bladder cancer upon determining the level of eIF4B higher than a reference level of eIF4B from healthy individuals; and
   (iv) administering surgery, chemotherapy, radiotherapy, or immunotherapy to the individual to treat bladder cancer.

2. The method of claim 1, wherein step (ii) comprises determining the level of eIF4B in a first bladder tissue sample at a first point in time and the level of eIF4B in a second bladder tissue sample at a second and later point in time.

3. The method of claim 2, further comprising comparing the levels of eIF4B determined at the different time points.

4. The method of claim 1, further comprising determining the level of at least one eIF in the bladder tissue sample, wherein the at least one eIF is selected from the group consisting of eIF1, eIF5A, eIF4G, eIF5B, and eIF6.

5. The method of claim 1, further comprising, prior to step (i), a step of obtaining the bladder tissue sample from the individual.

6. The method of claim 1, wherein the bladder cancer is selected from the group consisting of urothelial bladder cancer, squamous cell bladder cancer, adenocarcinoma, sarcoma, and small cell bladder cancer.

7. The method of claim 1, wherein the surgery comprises transurethral resection.

8. The method of claim 7, wherein the reference level is the level determined by measuring at least one reference bladder tissue sample from at least one healthy individual not suspected of having bladder cancer.

9. The method of claim 1, wherein the surgery comprises partial or complete removal of the bladder.

10. The method of claim 9, wherein the reference level is the level determined by measuring at least one reference bladder tissue sample from at least one healthy individual not suffering from bladder cancer.

11. The method of claim 1, wherein the surgery comprises urinary diversion.

* * * * *